US005609862A

United States Patent [19]
Chen et al.

[11] Patent Number: 5,609,862
[45] Date of Patent: *Mar. 11, 1997

[54] AMPHOLYTE TEROPOLYMERS PROVIDING SUPERIOR CONDITIONING PROPERTIES IN SHAMPOOS AND OTHER HAIR CARE PRODUCTS

[75] Inventors: Shih-Ruey T. Chen, Pittsburgh; Craig W. Vaughan, Freedom, both of Pa.

[73] Assignee: Calgon Corporation, Pittsburgh, Pa.

[ * ] Notice: The portion of the term of this patent subsequent to Mar. 22, 2011, has been disclaimed.

[21] Appl. No.: 87,839

[22] Filed: Jul. 1, 1993

Related U.S. Application Data

[63] Continuation of Ser. No. 723,001, Jun. 28, 1991, abandoned.

[51] Int. Cl.$^6$ .................. A61K 7/06; A61K 7/08
[52] U.S. Cl. .................. 424/70.11; 424/70.22; 424/70.27; 424/47; 424/DIG. 1; 424/DIG. 2; 132/203; 514/937; 514/944
[58] Field of Search .................. 514/944, 937; 424/78.02, 70, 71, 78.1, 78.12, DIG. 1, DIG. 2, 70.11, 70.22, 70.27, 47; 132/203

[56] References Cited

U.S. PATENT DOCUMENTS

| | | | |
|---|---|---|---|
| 3,986,825 | 12/1976 | Sokol | 424/70.11 |
| 4,131,576 | 12/1978 | Iovine et al. | 260/17.4 |
| 4,175,572 | 11/1979 | Hsiung et al. | 424/70.11 |
| 4,455,240 | 6/1984 | Costello | 526/295 |
| 4,460,477 | 7/1984 | Costello et al. | 252/8 |
| 4,484,631 | 11/1984 | Sherwood et al. | 166/274 |
| 4,533,708 | 8/1985 | Costello | 424/70.11 |
| 4,710,374 | 12/1987 | Grollier et al. | 424/70.22 |
| 4,719,099 | 1/1988 | Grollier | 424/47 |
| 4,803,071 | 2/1989 | Iovine et al. | 424/70.11 |
| 4,842,849 | 6/1989 | Grollier et al. | 424/70.22 |
| 4,859,458 | 8/1989 | Salamone et al. | 424/70.11 |
| 4,923,694 | 5/1990 | Shih et al. | 424/70.11 |
| 4,963,348 | 10/1990 | Bolich | 424/70.11 |
| 4,996,059 | 2/1991 | Grollier | 424/70.11 |
| 5,045,617 | 9/1991 | Shih et al. | 526/264 |

FOREIGN PATENT DOCUMENTS

| | | | |
|---|---|---|---|
| 308189 | 9/1988 | European Pat. Off. . | |
| 308190 | 9/1988 | European Pat. Off. . | |
| 353987 | 8/1989 | European Pat. Off. . | |
| 0331994 | 9/1989 | European Pat. Off. | 424/70.11 |
| 080976 | 6/1983 | Germany . | |
| 2113245 | 1/1983 | United Kingdom . | |

OTHER PUBLICATIONS

Sykes, et al, "The Use of Merquat Polymers In Cosmetics", 1980, pp. 62, 64, 66, 68, and 136.

Primary Examiner—Raj Bawa
Attorney, Agent, or Firm—Craig G. Cochenour

[57] ABSTRACT

Ampholyte terpolymer conditioning additives for hair care products are disclosed which improve wet and dry hair combability, especially detangling and reduced static flyaway, sheen, and fixative properties, especially curl retention. The ampholyte terpolymers may have a weight average molecular weight of from about 10 thousand to 10 million, and comprise (a) from at least 1 to as much as 95 weight percent of a nonionic monomer, (b) from at least 5 to as much as 80 weight percent of a cationic monomer, and (c) from at least 1 to as much as 75 weight percent of an anionic monomer. In a preferred embodiment, the amount of the cationic and anionic components is such that the overall % net charge of the ampholyte terpolymer is between −5.0 and +5.0. The ampholyte terpolymers are added to hair care product formulations in amounts ranging from 0.1–10% by weight. They are particularly compatible with anionic surfactant shampoos, providing clear formulations without the loss of conditioning properties described above.

19 Claims, No Drawings

AMPHOLYTE TEROPOLYMERS PROVIDING SUPERIOR CONDITIONING PROPERTIES IN SHAMPOOS AND OTHER HAIR CARE PRODUCTS

This is a continuation of application Ser. No. 07/723,001, filed on Jun. 28, 1991, now abandoned.

BACKGROUND OF THE INVENTION

1. Field of the Invention

The present invention relates to compositions and methods for treating hair in which a cosmetically acceptable medium is used which contains from 0.1–10% by weight of an ampholyte terpolymer. In particular, the cosmetically acceptable medium is an anionic surfactant-containing shampoo, and the ampholyte terpolymer exhibits good compatibility therewith in that the final solution is clear.

The surface properties of human hair are, of course, of basic interest in cosmetic science, and there has thus been a long-standing desire to discover ingredients which will beneficially affect the topical and bulk condition of this keratinous substrate. Such ingredients must have adequate adherent properties, so that they are not only adsorbed initially, but are also retained on exposure to water. This property is referred to as "substantivity", i.e., the ability of a material to be adsorbed onto the keratin of the hair and to resist removal by water rinse-off.

As indicated, human hair is composed of keratin, a sulfur-containing fibrous protein. The isoelectric point of keratin, and thus of the hair of which it is composed, is in the pH range of 3.2–4. Thus, at the pH of typical shampoo conditions, hair carries a net negative charge. Consequently, cationic polymers have long been used as conditioners in shampoo formulations, or as a separate treatment, in order to improve the wet and dry combability of the hair. The substantivity of the cationic polymers for negatively charged hair leads to film formation that facilitates detangling in wet hair combing and a reduction in static flyaway in dry hair combing. The cationic polymers also impart softness and suppleness to the hair.

It is a feature of the ampholyte terpolymers of the present invention that by varying the molar amounts and/or types of cationic components of the overall terpolymer, it is possible to adjust the cationic nature of the amphoteric polymer. By altering the mole percent charge, distribution of the cationic charge on the polymer backbone, and distance from the backbone (side chain length), one can achieve variations in the substantivity, conditioning properties, and static flyaway control of the resulting ampholyte terpolymer.

When cationic polymers are added to shampoos containing anionic surfactants, formation of highly surface active association complexes takes place which imparts improved foam stability to the shampoo. Maximum surface activity and foam stability, or lather, are achieved at near stoichiometric ratios of anionic sufactant:cationic polymer, where the complex is least water soluble. All cationic conditioners exhibit some incompatibility at some of these ratios. Compatibility gives a commercially more desirable clear formulation, while incompatibility leads to a haze or precipitation, which is aesthetically less desirable.

Hair fixative properties such as curl retention, are directly related to the film forming properties of the cationic monomers, as well as to molecular weight, with performance increasing with increasing molecular weight. However, the fixative properties conferred by the cationic monomers tend to have a reciprocal relationship to the other conditioning properties, i.e., good curl retention means that wet combability, for example, will suffer, and vice versa.

Nevertheless, the ampholyte terpolymers of the present invention give one the ability, by varying the proportions and individual character of the nonionic, cationic and anionic components, to balance the hydrophobic and hydrophilic characteristics of the overall ampholyte terpolymer, thereby permitting one to optimize the conditioning properties or fixative properties, or a mixture of both.

It is also possible, by varying the types and proportions of the nonionic, cationic and anionic components, especially the anionic components, of the ampholyte terpolymers of the present invention, to be able to adjust the acidic nature, e.g., the $pK_a$, of the anionic component of those terpolymers so as to more closely adjust the intrapolymer and polymer/hair interactions, and thereby favorably affect the resulting conditioning and fixative properties.

Surprisingly, it has been found that it is possible, by adjusting the weight proportions and types of the components of the ampholyte terpolymers of the present invention, to retain a desired balance of the beneficial conditioning properties conferred by each of those components. Thus, it is possible to keep the desired properties of substantivity, combability and feel, while at the same time improving anionic surfactant compatibility, curl retention, sheen, and static reduction properties. It is also possible to selectively optimize one or a subset of these conditoning properties, by proper proportioning of the components and their molecular weights. This may be a desired course of action responsive to an expression of consumer group preference for one or another of these various conditioning properties, depending on the makeup of that consumer group.

As already indicated, it is a preferred embodiment of the present invention to add the ampholyte terpolymers directly to an anionic surfactant-containing shampoo. Other embodiments are contemplated, however. Thus, excellent results have been achieved with treatments usually followed by rinsing, such as shampooing, but have also been achieved with treatments with lotions or creams followed by rinsing, which are used to obtain hair-conditioning effects and are applied before or after coloring, bleaching, shampooing, perming or straightening.

Thus, the compositions according to the present invention can also be used in the form of coloring products, setting lotions, blow-drying lotions, restructuring lotions or bleaching, perming or straightening products.

2. Brief Description of the Prior Art

Heretofore, hair conditioning additives have been largely of three different types: cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylaminoethylmethacrylate, and amino functional polydimethylsiloxane. Hydrolyzed animal protein has been frequently used as a hair conditioner. Also used are natural products such as collagen and casein. Suitable quaternary ammonium compounds include such products as stearyl dimethyl ammonium chloride.

Conditioning additives comprising copolymers of dimethyldiallylammonium chloride and other monomers are well known; see, e.g., EP 308189 (with acrylamide); EP 0 308 190 and U.S. Pat. No. 4,803,071 (with hydroxyethyl cellulose). The use of such polymers in cosmetics is also described in Sykes et al., *Drug Cosmet. Ind.*, 126(2), 62, 64, 66, 68, 136 (1980). Amphoteric betaines have also been employed in cosmetic compositions; see GB 2,113,245 which discloses use of betainized dialkylaminoalkyl-(meth)acrylate together with a cationic polymer.

The use of polymers of dimethyldiallylammonium chloride alone in hair treatment compositions is also known. See, e.g., U.S. Pat. Nos. 4,175,572 and 3,986,825.

While the use of various combinations of cationic, anionic and/or nonionic polymers as additives for hair conditioning compositions has been suggested heretofore, there has been no appreciation that a significant improvement in all of the desired hair conditioning properties could be obtained by employing an ampholyte terpolymer of the type used in the compositions and methods of the present invention.

For example, U.S. Pat. No. 4,859,458 discloses hair conditioning polymers containing alkoxylated nitrogen salts of sulfonic acid which may also include additional monomers that may be neutral, anionic and/or cationic. While these include acrylamide, acrylic acid and dimethyldiallylammonium chloride, there is no suggestion of the ampholyte terpolymers of the present invention.

EP 0 353 987 discloses polymers for water-rinsable personal care products including conditioning shampoos, comprising a cationic monomer including dimethyldiallylammonium chloride, a monomer that carries a pendant group $A_nR$ where n is 0 or a positive integer, A is ethyleneoxy and R is a hydrocarbyl group of 8 to 30 carbon atoms, and optionally a nonionic and/or an anionic monomer. However, there is no suggestion of the ampholyte terpolymers of the present invention.

U.S. Pat. No. 4,710,374 discloses compositions suitable for treating the hair comprising a cationic polymer including poly(dimethyldiallylammonium chloride), and an anionic latex, but there is no suggestion of the ampholyte terpolymers of the present invention.

U.S. Pat. No. 4,842,849 discloses compositions suitable for treating the hair comprising at least one cationic polymer including poly(dimethyldiallylammonium chloride), and at least one anionic polymer containing vinylsulfonic groups, optionally copolymerized with acrylamide. The cationic polymer may be an amphoteric polymer as defined, but none of these combinations suggest the ampholyte terpolymers of the present invention.

EP 0 080 976 discloses aqueous hair-cosmetic compositions containing a surface active polymeric acrylic-based quaternary ammonium salt, a monomeric or oligomeric ammonium salt, and a surface active nonionic, anionic or zwitterionic component. The ampholyte terpolymers of the present invention are not suggested.

The ampholyte terpolymers of the present invention are regarded as novel compositions of matter because of their unique properties, and their use as hair conditioning additives has not heretofore been suggested.

Terpolymers of acrylamide/dimethyldiallylammonium chloride/acrylic acid are disclosed in U.S. Pat. Nos. 4,455,240; 4,460,477; 4,484,631; and 4,533,708; however, nowhere is there a suggestion that those terpolymers might be used as conditioning additives for hair products.

A graft copolymer of acrylamide/acrylic acid/amylopectin/dimethyldiallylammonium chloride is disclosed in U.S. Pat. No. 4,131,576, but is only suggested for use as a pigment retention agent in papermaking.

The ampholyte terpolymers of the present invention represent a significant advance in the state of the hair conditioning art and afford properties which are a surprising improvement over those possessed by the hair conditioning additives in the prior art described above. In contrast to such additives, the ampholyte terpolymers of the present invention provide either an optimized combination of all hair conditioning properties, or else an optimized subset of such properties, which include: detangling, wet combability, wet feel, dry combability, dry feel, sheen, static flyaway control, and curl retention. A detailed demonstration of the dramatic improvement in these properties is set out further below.

SUMMARY OF THE INVENTION

The present invention relates to a composition for treating hair in which a cosmetically acceptable medium is used which contains from 0.1–10% by weight of an ampholyte terpolymer having a weight average molecular weight of from about 10 thousand to 10 million, comprising (a) from at least 1 to as much as 95 weight percent of a nonionic monomer, (b) from at least 5 to as much as 80 weight percent of a cationic monomer, and (c) from at least 1 to as much as 75 weight percent of an anionic monomer.

In a preferred embodiment, the amount of the cationic and anionic components is such that the overall percent net charge of the ampholyte *terpolymer is between −5.0 and +5.0. And in particular, the cosmetically acceptable medium is an anionic surfactant-containing shampoo, and the ampholyte terpolymer exhibits good compatibility therewith in that the final solution is clear.

The present invention also relates to a method of treating hair which comprises applying to hair a cosmetically acceptable medium containing from 0.1–10% by weight of an ampholyte terpolymer having a weight average molecular weight of from about 10 thousand to 10 million, comprising (a) from at least 1 to as much as 95 weight percent of a nonionic monomer, (b) from at least 5 to as much as 80 weight percent of a cationic monomer, and (c) from at least 1 to as much as 75 weight percent of an anionic monomer.

In a preferred embodiment, the amount of the cationic and anionic components of the ampholyte terpolymer is such that the overall % net charge of the ampholyte terpolymer is between −5.0 and +5.0. And in particular, the cosmetically acceptable medium is an anionic surfactant-containing shampoo, and the ampholyte terpolymer exhibits good compatibility therewith in that the final solution is clear.

The present invention further relates to a method of treating hair in conjunction with the shampooing thereof with an anionic sufactant-containing shampoo, so as to improve the conditioning thereof with respect to the properties of detangling, wet combability, wet feel, dry combability, dry feel, sheen, static flyaway control, and curl retention which comprises applying to hair a cosmetically acceptable medium containing from 0.1–10% by weight of an ampholyte terpolymer having a weight average molecular weight of from about 10 thousand to 10 million, comprising (a) from at least 1 to as much as 95 weight percent of a nonionic monomer, (b) from at least 5 to as much as 80 weight percent of a cationic monomer, and (c) from at least 1 to as much as 75 weight percent of an anionic monomer, wherein the amount of the cationic and anionic components is such that the overall % net charge of the ampholyte terpolymer is between −5.0 and +5.0, and wherein the ampholyte terpolymer exhibits good compatibility with the anionic sufactant-containing shampoo in that the final solution thereof is clear.

DETAILED DESCRIPTION OF THE INVENTION

As already indicated, the present invention relates to a composition for treating hair in which a cosmetically acceptable medium is used which contains from 0.1–10% by weight of an ampholyte terpolymer having a weight average molecular weight of from about 10 thousand to 10 million, comprising (a) from at least 1 to as much as 95 weight percent of a nonionic monomer, (b) from at least 5 to as much as 80 weight percent of a cationic monomer, and (c) from at least 1 to as much as 75 weight percent of an anionic monomer.

Components of the Ampholyte Terpolymers

Turning to each of the components of the ampholyte terpolymer in turn, the nonionic monomer comprises from 1 to 3 members independently selected from the group consisting of the following monomers and derivatives thereof:

| | |
|---|---|
| acrylamide (AM) | vinylacetate (VA) |
| N-alkylacrylamide (NAAM) | vinyl alcohol (VOH) |
| N-vinylpyrrolidinone (VP) | acrylate esters |
| methacrylamide (MAM) | allyl alcohol (AAlc) |

Derivatives of the above monomers are well known and those are useful in the present invention which provide the various conditioning and fixative properties described further herein. For example, N-alkylacrylamide and methacrylamide may be regarded as derivatives of acrylamide, and these together with other known derivatives of acrylamide suitable for use in the ampholyte terpolymers of the present invention may be represented by the following general formula:

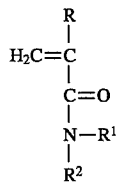

where R is H or $CH_3$; and $R^1$ and $R^2$ are independently H, $C_{1-4}$alkyl, $CH_2OCH_3$, $CH_2OCH_2CH(CH_3)_2$, $(CH_2CH_2O\text{---})_x\text{---}H$, where $x=1\text{--}50$, or phenyl, or together are $C_{3-6}$cycloalkyl.

The preferred acrylamide monomer is the simplest, i.e., that where R, $R_1$, and $R_2$ are all H.

The nonionic monomer portion of the ampholyte terpolymers of the present invention is usually present in an amount of from 1 to 95 weight percent of the total terpolymer. Preferably, this amount is from 5 to 80 weight percent, and most preferably, this amount is from 10 to 50 weight percent. However, in the case of the monomers N-alkylacrylamide, vinyl acetate, vinyl alcohol, and acrylate esters, solubility problems are created when the proportion of these anionic monomers is at the higher end of the ranges recited above for the overall ampholyte terpolymer. Thus, the N-alkylacrylamide monomers should be present in amounts of from 1 to 10% by weight; and the vinyl acetate, vinyl alcohol, and acrylate esters monomers should be present in amounts of from 1 to 30% by weight as components of the overall ampholyte terpolymer.

As will be appreciated by the synthetic polymer chemist, the vinyl alcohol monomer will most conveniently be generated as a monomer simply by hydrolysis of vinyl acetate. Similarly, acrylic acid and methacrylic acid may be conveniently introduced into the terpolymer by hydrolysis of acrylamide and methacrylamide, respectively.

The acrylamide and other nonionic components of the ampholyte terpolymers of the present invention contribute to the film forming capacity of the total terpolymer and thus improve curl retention. They also improve the static flyaway control of the overall terpolymer.

Since, in a preferred embodiment of the present invention the amounts of cationic and anionic components are such that the net charge of the overall terpolymer is near zero, there is a tendency in such preferred terpolymers to form water insoluble polysalt complexes. The presence of acrylamide and the other nonionic monomer components serve to enhance the water solubility of the terpolymers in those situations.

It has also been discovered that, surprisingly, when the weight percent of acrylamide and other nonionic monomer components is reduced from about 50 to about 25 weight percent, while the balance of cationic and anionic components stays approximately the same, there is a substantial improvement in the wet hair conditioning properties of detangling, combability and feel. Consequently, the most preferred range of weight percents for the acrylamide and other nonionic components is from 10 to 50.

The next component of the ampholyte terpolymers of the present invention is the cationic monomer, e.g., derivatives of diallylamine, especially dimethyldiallylammonium chloride (DMDAAC). More generally, the cationic monomer comprises 1 or 2 members independently selected from the group consisting of the following monomers and derivatives thereof:

dimethyldiallylammonium chloride (DMDAAC)
diallylamine (DAA)
methyldiallylamine (MDAA)
N,N-dialkyldiallylammonium chloride ($R_1$, $R_2$ higher than $CH_3$ in the formula below)
dimethylaminoethylmethacrylate (DMAEM)
methacyloyloxyethyl trimethylammonium chloride (METAC)
methacyloyloxyethyl trimethylammonium metyl sulfate (METAMS)
acryloyloxyethyl trimethylammonium chloride (AETAC)
dimethylaminopropylmethacrylamide (DMAPMA)
methacrylamidopropyl trimethylammonium chloride (MAPTAC)

Derivatives of the above cationic monomers are well known and those are useful in the present invention which provide the various conditioning and fixative properties described further herein. For example, dimethyldiallylammonium chloride, methyldiallylamine, and N,N-dialkyldiallylammonium chloride may be regarded as derivatives of diallylamine, and these together with other known derivatives of diallylamine suitable for use in the ampholyte terpolymers of the present invention may be represented by the following general formula:

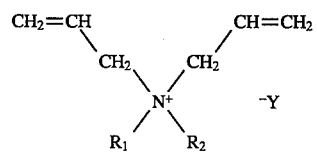

where $R_1$ and $R_2$ are independently H or $C_{1-12}$alkyl. The moiety $^-Y$ is a suitable anion, such as halide, preferably $^-Cl$, but also including sulfate, and so forth. It is within the skill of the artisan to choose such an anion. The preferred cationic monomer component of the ampholyte terpolymers of the present invention is dimethyldiallylammonium chloride (DMDAAC), i.e., where $R_1$ and $R_2$ are $CH_3$.

The cationic monomer portion of the ampholyte terpolymers of the present invention is present in an amount of from 5 to 80 weight percent of the total terpolymer. Preferably, this amount is from 15 to 60 weight percent. However, in the case of the monomers N,N-dialkyldiallylammonium chloride, i.e., where $R_1$ and $R_2$ are alkyl higher than methyl in the formula above, solubility problems are created when the proportion of these cationic monomers is at the higher end of the ranges recited above for the overall ampholyte terpolymer. Thus, the N,N-dialkyldiallylammonium chloride monomers should be present in amounts of from 1 to 10% by weight as components of the overall ampholyte terpolymer.

The dimethyldiallylammonium chloride and other cationic monomers contribute to all of the hair conditioning properties except for curl retention. As cationic monomers they possess the inherent substantivity necessary for the overall terpolymer to function. They also provide the basic improvement in derangling, wet and dry hair combability, sheen and feel, and control of static flyaway. However the dimethyldiallylammonium chloride and other cationic monomers do not possess good film forming properties, and thus do not play any substantial role in improving curl retention.

The final component of the ampholyte terpolymers of the present invention is the anionic monomer, e.g., acrylic acid (AA). More generally, the anionic monomer comprises 1 or 2 members independently selected from the group consisting of the following monomers and derivatives thereof:

acrylic acid (AA)
methacrylic acid (MAA)
2-acrylamido-2-methylpropanesulfonic acid (AMPSA)
crotonic acid (CA)
sodium vinyl sulfonate (SVS)
acrylamidoglycolic acid (AGly)
2-acrylamido-2-methylbutanoic acid (AMBA)
2-acrylamido-2-methylpropanephosphonic acid (AMPPA)
sodium vinyl phosphonate (SVP)
allyl phosphonic acid ((APA)

Derivatives of the above anionic monomers are well known and those are useful in the present invention which provide the various conditioning and fixative properties described further herein. For example, methacrylic acid may be regarded as a derivative of acrylic acid, and it together with other known derivatives of acrylic acid suitable for use in the ampholyte terpolymers of the present invention may be represented by the following general formula:

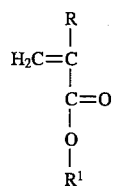

where R is H or $CH_3$; and $R^1$ is $X^+$, H $C_{1-4}$alkyl, $CH_2CH_2OH$, $(CH_2CH_2O-)_x-H$, where x=1–50, or phenyl, and $X^+$ is a suitable cation forming a salt of the carboxylic acid, such as sodium, potassium, ammonium, monoethaolamine, etc., all of which are well known and within the ordinary skill of the artisan to choose.

The acrylic acid and other anionic monomer components of the ampholyte terpolymers of the present invention are present in an amount of from 1 to 75 weight percent of the total terpolymer. Preferably, this amount is from 5 to 40 weight percent. However, in the case of the monomers acrylamidoglycolic acid, solubility problems are created when the proportion of these anionic monomers is at the higher end of the ranges recited above for the overall ampholyte terpolymer. Thus, the acrylamidoglycolic acid monomers should be present in amounts of from 1 to 10% by weight as components of the overall ampholyte terpolymer.

The acrylic acid and other anionic monomers recited above, along with the acrylamide, contribute to the film forming capacity of the total terpolymer and thus improve curl retention. In amounts as little as 1–2 weight percent, the acrylic acid and other anionic monomers measurably improve the compatibility of the overall terpolymer with the anionic surfactant of which a typical shampoo is made. It has also been found that the acrylic acid and other anionic monomers add to the improvement of all of the hair conditioning properties already provided by the cationic component as discussed above. This result is unexpected, and is another indication of the unexpected properties of the ampholyte terpolymers of the present invention.

A Preferred Subclass of Ampholyte Terpolymers

A unique feature of the ampholyte terpolymers of the present invention is that it is possible to keep the desired properties of substantivity, combability and feel, while at the same time improving anionic surfactant compatibility, curl retention, sheen, and static reduction properties. This can be achieved most readily by using a preferred embodiment of the present invention which is the subclass of ampholyte terpolymers wherein the cationic and anionic components are present in mole percent amounts such that the % net charge of the overall ampholyte terpolymez is between −5.0 and +5.0. It is desirable that the % net charge be as near to zero as possible. The % net charge of the overall ampholyte terpolymez can be readily determined in accordance with the following equation:

% Net Charge=Mole % Cationic Monomer—Mole % Anionic Monomer

It is possible to selectively optimize one or a subset of the desired conditoning properties described above, by proper proportioning of the nonionic, cationic and anionic components of the ampholyte perpolymers and their molecular weights. This may be a desired course of action responsive to an expression of particular consumer group preference for one oranother of these various conditioning properties, depending on the makeup of that particular consumer group.

Specific Ampholyte Terpolymers

Examples of specific preferred ampholyte terpolymers within the scope of the present invention are the following:

| | |
|---|---|
| AM/DMDAAC/AGly | acrylate esters/DMDAAC/AA |
| AM/DMDAAC/AMBA | AM/DMDAAC/AA/AMPSA/AMPPA |
| AM/DMDAAC/APA | acrylate esters/DMDAAC/AMBA |
| AM/DMDAAC/AMPPA | AM/DMDAAC/SVP |
| AAlc/DMDAAC/AA | |

Examples of specific more preferred ampholyte terpolymers within the scope of the present invention are the following:

| | |
|---|---|
| AM/MDAA/AA | VP/DAA/AA |
| VP/METAMS/MAA/AA | VP/DMDAAC/AMPSA |
| MAM/METAMS/MAA | AM/VP/DMDAAC/AMPSA |
| AM/VP/METAMS/MAA | AM/VP/DMDAAC/AA/AMPSA |

| | |
|---|---|
| AM/VP/METAMS/MAA/ AA | AM/DMDAAC/AETAC/AA |
| VP/AETAC/AA | AM/DMDAAC/DMAEM/AA |

Examples of specific most preferred ampholyte terpolymers within the scope of the present invention are the following:

| | |
|---|---|
| AM/DMDAAC/MAA | AM/MAPTAC/AA |
| AM/DMDAAC/CA | VP/DMDAAC/AA |
| AM/DMDAAC/SVS | AM/VP/DMDAAC/AA |
| AM/DAA/AA | AM/MAM/DMDAAC/AA |
| AM/DAA/MAA | AM/NAAM/DMDAAC/AA |
| AM/DMAEM/AA | AM/DAA/AMPSA |
| AM/AETAC/AA | AM/VA/VOH/DMDAAC/AA |
| AM/METAMS/MAA | VP/METAMS/MAA |

Molecular Weights

The molecular weight of the ampholyte terpolymers of the present invention may be within the broad range of from about 10 thousand to about 10 million. The molecular weights of most of the specific terpolymers described herein are within the range of about 4 to 8 million. However, it is generally conceded that for polymers used in hair conditioning, molecular weights over about 1 million add little to the effectiveness of those polymers in terms of hair conditioning properties, with the possible exception of curl retention. At the other end of the scale, polymers with relatively low molecular weights may also be effective in providing hair conditioning properties. For example, a commercial hair conditioning polymer of the Polymer JR (Reg. TM) series, has a molecular weight of about 30 thousand. The ampholyte terpolymers of the present invention are also useful in weight average molecular weight ranges below 1 million, and even below 100 thousand, although generally the preferred molecular weight range will be from about 500 thousand to 5 million.

Reduced viscosity (dl/g) is used herein as an approximate measure of the weight average molecular weight of the ampholyte terpolymers of the present invention. Such values represent a capillary viscosity measured with a Ubbelohde Capillary Viscometer at 0.05% concentration of polymer in a 1M NaCl solution, pH 7, at 30° C. The resulting value is calculated in accordance with methods well known in the art.

Preparation (Polymerization)

The ampholyte terpolymers of the present invention may be prepared in a straightforward manner by using the process described immediately below.

For each terpolymer composition the appropriate weights of aqueous nonionic component, e.g., acrylamide, and cationic component, e.g., DMDAAC, monomers are charged to a glass reactor equipped with stirring. The volume of anionic component, e.g., acrylic acid, monomer to be added is diluted first with deionized water and then added to the reactor with vigorous stirring to give a total monomer concentration of 14–20%. The monomer mixture is adjusted to pH 6.5 with dilute NaOH, heated to 55° C., and purged with nitrogen for at least thirty minutes. Polymerization is initiated by adding $5 \times 10^{-2}$ mole % of sodium persulfate and $2.4 \times 10^{-3}$ mole % of sodium bisulfite. After the peak exotherm is reached, additional dilution water and sodium bisulfite are added to scavenge any residual monomer and to dilute the final product to 4–8% polymer solids.

As already noted further above, in the case of certain anionic components such as acrylic acid and methacrylic acid may be introduced into the terpolymer by adding the corresponding nonionic components acrylamide and methacrylamide, respectively, and then hydrolyzing these once they are a part of the terpolymer, or in the course of its preparation, to give the desired amount of corresponding anionic component in the terpolymer final product. It has also been mentioned that the nonionic component vinyl alcohol (VOH) is most conveniently prepared by hydrolysis of the corresponding vinyl acetate (VA), so that the latter is the component introduced during polymerization, to be hydroyzed later to the vinyl alcohol.

Cosmetically Acceptable Media

The ampholyte terpolymers of the present invention are used as compositions for treating hair by incorporating them in a cosmetically acceptable medium in amounts of from 0.1–10% by weight of said terpolymer, and preferably in an amount of from 0.5 to 5% by weight of said terpolymer.

These compositions can be presented in various forms, i.e., various cosmetically acceptable media, such as a liquid, cream, emulsion, gel, thickening lotion or powder; they can contain water and also any cosmetically acceptable solvent, in particular monoalcohols, such as alkanols having 1 to 8 carbon atoms, like ethanol, isopropanol, benzyl alcohol and phenylethyl alcohol, polyalcohols, such as alkylene glycols, like glycerins, ethylene glycol and propylene glycol, and glycol ethers, such as mono-, di- and tri-ethylene glycol monoalkyl ethers, for example ethylene glycol monomethyl ether, ethylene glycol monomethyl ether and diethylene glycol monomethyl ether, used singly or in a mixture. These solvents can be present in proportions of up to as much as 70% by weight, relative to the weight of the total composition.

These compositions can also be packaged as an aerosol, in which case they can be applied either in the form of an aerosol spray or in the form of an aerosol foam.

As the propellant gas for these aerosols, it is possible to use, in particular, dimethyl ether, carbon dioxide, nitrogen, nitrous oxide and volatile hydrocarbons, such as butane, isobutane, propane and, possibly, chlorinated and fluorinated hydrocarbons, although the latter are falling into increasing environmental disfavor.

Preferred compositions can also contain electrolytes, such as aluminum chlorhydrate, alkali metal salts, e.g., sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium.

These compositions can also be presented in the form of a powder or of lyophilisates to be diluted before use.

The compositions according to the present invention can contain any other ingredient normally used in cosmetics, such as perfumes, dyestuffs which can serve to color the composition itself or the fibres of the hair, preservatives, sequestering agents, thickeners, silicones, softeners, foam synergistic agents, foam stabilisers, sun filters, peptising agents and also anionic, non-ionic, cationic or amphoteric surface-active agents or mixtures thereof.

These compositions can be used, in particular, in the form of a shampoo, a rinsing lotion, a cream or a treatment product which can be applied before or after coloring or bleaching, before or after shampooing, before or after perming or before or after straightening, and can also adopt the form of a coloring product, a setting lotion, a brushing lotion, a bleaching product, a perming product or a straightening product.

A particularly preferred embodiment consists of use in the form of a shampoo for washing the hair.

In this case, these compositions contain anionic, cationic, nonionic or amphoteric surface-active agents typically in an amount from 3 to 50% by weight, preferably 3 to 20%, and their pH is 3 to 10.

A list of the surface-active agents which can be used according to the invention is given in U.S. Pat. Nos. 4,240,450; 4,445,521; and 4,719,099.

Another preferred embodiment consists of use in the form of a rinsing lotion to be applied mainly before or after shampooins. These lotions are typically aqueous or aqueous-alcoholic solutions, emulsions, thickened lotions or gels. If the compositions are presented in the form of an emulsion, they can be nonionic, anionic or cationic. The nonionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially carbopol, xanthan gums, sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is suitably 0.05 to 15% by weight. If the compositions are presented in the form of a styling lotion, shaping lotion or setting lotion, they generally comprise, in aqueous, alcoholic or aqueous-alcoholic solution, the ampholyte tezpolymers defined above.

If the compositions of the invention are intended for use in the dyeing of keratin fibres, and in particular human hair, they contain at least one oxidation dyestuff precursor and/or one direct dyestuff, in addition to the ampholyte terpolymer. They can also contain any other adjuvant normally used in this type of composition.

The pH of the dyeing compositions is generally 7 to 11 and can be adjusted to the desired value by adding an alkalizing agent.

The composition according to the present invention can also be used for waving or straightening the hair. In this case, the composition contains, in addition to the ampholyte terpolymer, one or more reducing agents and, if appropriate, other adjuvants normally used in this type of composition; such compositions are intended for use conjointly with a neutralizing composition.

EXAMPLES OF PREFERRED EMBODIMENTS

The following examples demonstrate hair conditioning improvement results which can be obtained with specific ampholyte terpolymers of the present invention, but are not intended to in any way limit the scope of the present invention.

EXAMPLE 1

Wet Hair: Detangling, Combability and Feel

The following procedures are used to evaluate wet hair detangling, combability and feel:

1. Eighteen 2 grams tresses of bleached hair (supplied by Ruth L. Weintraub Co., Inc., 420 Madison Avenue, New York, N.Y. 10017), 8 inches in length, are prepared for testing. The ends are trimmed to equal lengths (6 inches; length=L); and the root end of the hair is placed into a clamp.
2. All of the tresses are washed in clean denatured alcohol (100%), by dipping each tress in the denatured alcohol and swirling 3 times. The tresses are allowed to dry by hanging on a peg board, at room temperature for 1 hour.
3. Using 6 tresses per treatment, each tress is immersed in one of the following three test solutions (the pH of these solutions is adjusted to 6.0±0.1 with citric acid or NaOH):

a) Terpolymer solution, 0.5% Solids b) Gafquat 755N (Reg. TM) solution, 0.5% Solids c) deionized (DI) water.

Each tress is allowed to soak in the solution for 3 minutes and is then rinsed under running deionized water for 2 minutes.
4. After the 2 minute rinse, each trees is evaluated for detangling, wet hair combability and wet hair feel. The detangling is evaluated by holding the clamp of the tress in one hand and using the other hand to comb the tress twice with the coarse end of the comb. The tress is then combed 5 times to remove all the tangles and the tress is combed twice with the fine end of the comb to evaluate wet hair comb. The tresses are evaluated and rated for detangling and wet hair combability in accordance with the following scale:

4=Excellent=No snags

3=Very Good=Very few snags

2=Good=Few snags

1=Fair=Many snags

0=Poor=Very many snags

The wet hair feel is evaluated by the subjective feel to the fingers of each tress. The combs [Goody (Reg. TM), H. Goodman & Sons, Inc., NY 10001] used for these tests are 7¼"×1½". The teeth on the course end of the comb are spaced ⅛" apart and the teeth on the fine end of the comb are spaced 1/16" apart.

The average of the results obtained in these tests are illustrated in the following table of values, in which WH=Wet Hair, DT=Derangling, and COMB=Combability:

TABLE 1

| SAMPLE NO. | WT. % POLYMER COMPOSITION | | | WH DT | WH COMB | WH FEEL |
|---|---|---|---|---|---|---|
| | AM | DMDAAC | AA | | | |
| 23 | 50 | 20 | 30 | 1 | 2 | 2 |
| 25 | 60 | 20 | 20 | 2 | 2 | 2 |
| 27 | 77 | 16 | 7 | 4 | 4 | 4 |
| 35 | 25 | 50 | 25 | 4 | 4 | 4 |
| 37 | 25 | 5 | 70 | 0 | 0 | 0 |
| 39 | 75 | 5 | 20 | 2 | 2 | 2 |
| 43 | 50 | 5 | 45 | 0 | 0 | 0 |
| 59 | 50 | 40 | 10 | 4 | 4 | 4 |
| 61 | 50 | 35 | 15 | 2 | 3 | 3 |
| 63 | 50 | 30 | 20 | 1 | 2 | 2 |
| 90 | 54 | 40 | 6 | 4 | 4 | 4 |
| GAFQUAT 755N (average) | | | | 4 | 4 | 4 |
| DI WATER (average) | | | | 0 | 0 | 0 |

EXAMPLE 2

Curl Retention

After the procedures are carried out as described in Example 1, the following procedures are used to evaluate curl retention:

5. A "curl paper" [Goody (Reg. TM), H. Goodman & Sons, Inc., N.Y. 10001] is folded around each hair tress, close to the clamp, and slid down the hair to cover all loose ends. The end of the hair tress is set on the left edge of the roller [medium snap-over roller $^{11}/_{16}$" diameter, Sekine (Reg. TM) Corporation, New York, N.Y. 10003], and is wound three times around the roller so that it ended up on the right hand edge of the roller. When all of the tresses had been treated, the entire rack of tresses is placed in a 50% relative humidity room and allowed to set overnight (at least 12 hours).
6. After this 12 hour set period, a humidity chamber is placed in a 50% relative humidity room. The atmosphere in the humidity chamber is then raised to 70% relative humidity (approx. 30 minutes) by blowing air over a 20% (w/w) solution of aqueous ammonium chloride and into the humidity chamber.
7. The rollers are then removed from the tresses.
8. The initial lengths of all the tresses are recorded as the length from the clamp to the bottom of the curl (initial length=$L_0$).
9. The rack of curls is then placed in the humidity chamber at 70% relative humidity for 15 minutes.
10. The length ($L_t$) of each tress (from the clamp to the bottom of the curl) is then measured every 15 minutes for 2 hours.
11. The curl retention is calculated using the following formula:

$$\% \text{ Curl Retention} = \frac{L - L_t}{L - L_0} \times 100$$

The results obtained from these tests are illustrated in the following table of values:

TABLE 2

| SAMPLE | WT. % POLYMER COMPOSITION | | | AVERAGE CURL RETENTION @ | |
|---|---|---|---|---|---|
| NO. | AM | DMDAAC | AA | 60 (min) | 120 (min) |
| 23 | 50 | 20 | 30 | 59.7 | 50.2 |
| 25 | 60 | 20 | 20 | 60.2 | 49.8 |
| 27 | 77 | 16 | 7 | 78.0 | 66.0 |
| 35 | 25 | 50 | 25 | 57.2 | 49.8 |
| 37 | 25 | 5 | 70 | 58.2 | 45.6 |
| 39 | 75 | 5 | 20 | 51.5 | 44.4 |
| 43 | 50 | 5 | 45 | 60.9 | 49.3 |
| 59 | 50 | 40 | 10 | 61.3 | 49.1 |
| 61 | 50 | 35 | 15 | 63.1 | 53.7 |
| 63 | 50 | 30 | 20 | 64.2 | 53.5 |
| 90 | 54 | 40 | 6 | 68.0 | 58.0 |
| GAFQUAT 755N (average) | | | | 64.4 | 53.9 |
| DI WATER (average) | | | | 53.6 | 43.8 |

EXAMPLE 3

Dry Hair: Combability, Feel and Sheen

The following procedures, which follow those carried out as described above in Examples 1 and 2, are used to evaluate dry hair combability, feel and sheen:

12. The rack of tresses used for the curl retention evaluations described in the previous example is removed from the humidity chamber and placed on a lab bench. Then, 8 panelists evaluated the 3 sets of 6 tresses for "ease of dry combing," "feel of hair," and "sheen or luster." Each panelist rates each tress for the preceding categories according to the following rating scale:

Poor=0; Fair=1; Good=2; Very Good=3; Excellent=4.

The results obtained from these evaluations are illustrated in the following table of values, in which DH=Dry Hair and COMB=Combability:

TABLE 3

| SAMPLE | WT. % POLYMER COMPOSITION | | | DH | DH | |
|---|---|---|---|---|---|---|
| NO. | AM | DMDAAC | AA | COMB | FEEL | SHEEN |
| 23 | 50 | 20 | 30 | 2.13 | 2.38 | 2.13 |
| 25 | 60 | 20 | 20 | 2.63 | 2.75 | 2 |
| 27 | 77 | 16 | 7 | 3.25 | 2.75 | 3.00 |
| 35 | 25 | 50 | 25 | 3.63 | 3.38 | 3 |
| 37 | 25 | 5 | 70 | 2.88 | 2.75 | 2.88 |
| 39 | 75 | 5 | 20 | 2.75 | 2.25 | 1.25 |
| 43 | 50 | 5 | 45 | 2.5 | 2.75 | 2.75 |
| 59 | 50 | 40 | 10 | 2.38 | 2.38 | 2.38 |
| 61 | 50 | 35 | 15 | 3.63 | 3 | 2.63 |
| 63 | 50 | 30 | 20 | 2.63 | 2.13 | 1.88 |
| 90 | 54 | 40 | 6 | 3.13 | 2.75 | 2.50 |
| GAFQUAT 755N (average) | | | | 2.54 | 2.60 | 2.37 |
| DI WATER (average) | | | | 2.64 | 2.69 | 2.76 |

EXAMPLE 4

Static Flyaway Control

The following procedures, which follow those carried out as described above in Examples 1, 2 and 3, are used to evaluate control of static flyaway:

13. When the preceding panelist evaluations are complete, one tress from each set (1-terpolymer, 1-Gafquat and 1-DI water) is wet under running DI water and combed until no tangles remained. These tresses are placed on a smaller peg board and put in the 50% relative humidity room overnight.
14. Each of the tresses is then placed on a peg board in front of a protractor. The tresses are combed 20 times, with the same stroke each time, and the angle of the hair is recorded. The static angle of the hair is determined by the hair strand which produces the largest angle for that tress.

The results obtained from this test are illustrated in the following table of values:

TABLE 4

| SAMPLE | WT. % POLYMER COMPOSITION | | | STATIC |
|---|---|---|---|---|
| NO. | AM | DMDAAC | AA | ANGLE (degrees) |
| 23 | 50 | 20 | 30 | 35 |
| 25 | 60 | 20 | 20 | 15 |
| 27 | 77 | 16 | 7 | 25 |
| 35 | 25 | 50 | 25 | 10 |
| 37 | 25 | 5 | 70 | 35 |
| 39 | 75 | 5 | 20 | 10 |
| 43 | 50 | 5 | 45 | 30 |
| 59 | 50 | 40 | 10 | 60 |
| 61 | 50 | 35 | 15 | 35 |
| 63 | 50 | 30 | 20 | 45 |
| 90 | 54 | 40 | 6 | 65 |
| GAFQUAT 755N (average) | | | | 55 |
| DI WATER (average) | | | | 37 |

The following examples illustrate various cosmetically acceptable media for preparing hair care compositons using the ampholyte terpolymers of the present invention. In those Examples, the following terpolymer abbreviations are used:

Polyampholyte A:

| By weight: | 50% Acrylamide |
| | 35% DMDAAC |
| | 15% Methacrylic Acid |

Polyampholyte B:

| By weight: | 50% Acrylamide |
| | 30% MAPTAC |
| | 20% Acrylic Acid |

Polyampholyte C:

| By weight: | 50% N-Vinylpyrrolidinone |
| | 40% DMDAAC |
| | 10% Acrylic Acid |

EXAMPLE 5

| Creme Rinse | |
|---|---|
| WT. % | INGREDIENT |
| 93.1 | $H_2O$ |
| 1.2 | Cetyl Alcohol |
| 0.8 | Stearyl Alcohol |
| 1.0 | Sorbitan Oleate |
| 0.4 | Polysorbate-85 |
| 1.0 | Distearyldiammonium Chloride |
| 2.5 | Polyampholyte B |

In this formulation, the ampholyte terpolymer stabilizes an otherwise unstable composition. The ampholyte terpolymer also improves combability, hair feel, and provides a feeling of increased hair body. Similar results would be expected at ampholyte terpolymer concentrations of 0.1 to 10.0% by weight.

EXAMPLE 6

| Shampoo | |
|---|---|
| WT. % | INGREDIENT |
| 28.50 | Water |
| 32.30 | Ammonium Lauryl Sulfate |
| 31.40 | Ammonium Laureth Sulfate |
| 4.25 | Ammonium Dodecylbenzene Sulfonate |
| 3.40 | Lauramide DEA |
| 0.15 | Disodium EDTA |
| 3.0 | Polyampholyte A |

The ampholyte terpolymer in this product formulation is responsible for a better feeling shampoo with thicker feeling lather. The hair is easier to comb and has a feeling of greater body. Similar results would be expected at ampholyte terpolymer concentrations of 0.1 to 10.0% by weight.

EXAMPLE 7

| Creme Type Rearranger | |
|---|---|
| WT. % | INGREDIENT |
| 68.95 | $H_2O$ |
| 6.00 | Sodium Lauryl Sulfate |
| 7.90 | Cetearyl Alcohol and Ceteareth-20 |
| 6.00 | Cetyl Alcohol and Ceteareth-30 |
| 1.50 | Ethylene Glycol Monostearate |
| 0.15 | Sodium Dihydroxyethylglycinate |
| 7.50 | Ammonium Thioglycolate (60%) |
| 2.00 | Aqua Ammonia |
| 4.00 | Polyampholyte C |

This type of product formulation is applied to extremely curly hair and is combed into the hair. Hair treated in this way will be straightened. The presence the ampholyte terpolymer makes the hair noticeably easier to comb. Effective amounts of ampholyte terpolymer in this type of product will be from 0.20% to 15.00% by weight.

EXAMPLE 8

| Hair Styling Glaze | |
|---|---|
| WT. % | INGREDIENT |
| 88.4% | Water |
| 1.10 | Hydroxypropyl Methylcellulose |
| 0.50 | Quaternium-80 |
| 10.00 | Polyampholyte B |

The ampholyte terpolymer in this formulation provides curl and style retention, and the ampholyte terpolymer should be effective for this purpose at concentrations of 0.5% to 20.0% by weight.

EXAMPLE 9

| Permanent Wave Neutralizer | |
|---|---|
| WT. % | INGREDIENT |
| 91.92 | $H_2O$ |
| 0.20 | Pentasodium Pentatate |
| 0.180 | Citric Acid |
| 5.70 | Hydrogen Peroxide (35%) |
| 2.0 | Polyampholyte C |

The ampholyte terpolymer in this product formulation imparts conditioning to and improves combability of hair. The ampholyte terpolymer should be effective at concentrations of 0.1% to 10% by weight or more.

EXAMPLE 10

| Hair Spray | |
|---|---|
| WT. % | INGREDIENT |
| 92.00 | Water |
| 1.00 | Acetamide MEA |
| 1.00 | Glycerin |
| 3.00 | Vinylcaprolactam/PVP/Dimethylaminoethylmethacrylate polymer |
| 3.00 | Polyampholyte A |

The ampholyte terpolymer in this formulation increases the style holding properties while improving the flexibility of the second polymer. Similar results should be obtained at ampholyte terpolymer concentrations of 0.3% to 10.0% by weight.

EXAMPLE 11

| Hair Styling Gel | |
|---|---|
| WT. % | INGREDIENT |
| 91.75 | H₂O |
| 0.375 | Carbomer - 940 |
| 0.625 | Triethanolamine |
| 0.10 | Trisodium EDTA |
| 5.0 | PVP |
| 0.2 | Laureth-23 |
| 0.2 | Oleth-20 |
| 0.25 | Hexylene Glycol |
| 1.50 | Polyampholyte A |

The ampholyte terpolymer in this product formulation provides increased curl and style retention along with increased flexibility of the hair fixative film.

What is claimed is:

1. A composition for treating hair in which a cosmetically acceptable medium is used which contains from 0.1–10% by weight of a water soluble ampholyte terpolymer having a weight average molecular weight of from about 10 thousand to 10 million, comprising:

(a) from at least 1 to as much as 95 weight percent of a nonionic monomer comprising from 1 to 3 members independently selected from the group consisting of the following monomers:

| acrylamide (AM) | vinylacetate (VA) |
|---|---|
| N-alkylacrylamide (NAAM) | vinyl alcohol (VOH) |
| | acrylate esters |
| methacrylamide (MAM) | allyl alcohol (AAlc) |

(b) from at least 5 to as much as 80 weight percent of a cationic monomer comprising 1 or 2 members independently selected from the group consisting of the following monomers:
   dimethyldiallylammonium chloride (DMDAAC)
   diallylamine (DAA)
   methyldiallylamine (MDAA)
   N,N-dialkyldiallylammonium chloride
   dimethylaminoethylmethacrylate (DMAEM)
   methacyloyloxyethyl trimethylammonium chloride (METAC)
   methacyloyloxyethyl trimethylammonium metyl sulfate (METAMS)
   acryloyloxyethyl trimethylammonium chloride (AETAC)
   dimethylaminopropylmethacrylamide (DMAPMA)
   methacrylamidopropyl trimethylammonium chloride (MAPTAC) and (c) from at least 1 to as much as 75 weight percent of an anionic monomer comprising 1 or 2 members independently selected from the group consisting of the following monomers:
   acrylic acid (AA)
   methacrylic acid (MAA)
   2-acrylamido-2-methylpropanesulfonic acid (AMPSA)
   crotonic acid (CA)
   sodium vinyl sulfonate (SVS)
   acrylamidoglycolic acid (AGly)
   2-acrylamido-2-methylbutanoic acid (AMBA)
   2-acrylamido-2-methylpropanephosphonic acid (AMPPA)
   sodium vinyl phosphonate (SVP)
   allyl phosphonic acid (APA)
wherein the amounts of the cationic and the anionic components are such that the overall % net charge of the ampholyte terpolymer is between about −5.0 and +5.0.

2. A composition according to claim 1 wherein the weight percent of the nonionic component is from 10 to 80, the weight percent of the cationic component is from 15 to 60, and the weight percent of the anionic component is from 5 to 40.

3. A composition according to claim 1 wherein the ampholyte terpolymer is a member selected from the group consisting of:

| | |
|---|---|
| AM/DMDAAC/AGly | acrylate esters/DMDAAC/AA |
| AM/DMDAAC/AMBA | AM/DMDAAC/AA/AMPSA/AMPPA |
| AM/DMDAAC/APA | acrylate esters/DMDAAC/AMBA |
| AM/DMDAAC/AMPPA | AM/DMDAAC/SVP |
| AAlc/DMDAAC/AA | |
| AM/MDAA/AA | |
| MAM/METAMS/MAA | |
| | AM/DMDAAC/AETAC/AA |
| | AM/DMDAAC/DMAEM/AA |
| AM/DMDAAC/MAA | AM/MAPTAC/AA |
| AM/DMDAAC/CA | |
| AM/DMDAAC/SVS | |
| AM/DAA/AA | AM/MAM/DMDAAC/AA |
| AM/DAA/MAA | AM/NAAM/DMDAAC/AA |
| AM/DMAEM/AA | AM/DAA/AMPSA |
| AM/AETAC/AA | AM/VA/VOH/DMDAAC/AA |
| AM/METAMS/MAA. | |

4. A composition according to claim 1 wherein the ampholyte terpolymer has a molecular weight of from about 500 thousand to about 5 million.

5. A composition according to claim 1 wherein the cosmetically acceptable medium is an anionic surfactant-containing shampoo.

6. A method of treating hair which comprises applying to said hair a cosmetically acceptable medium containing from 0.1–10% by weight of a water soluble ampholyte terpolymer having a weight average molecular weight of from about 10 thousand to 10 million, comprising:

(a) from at least 1 to as much as 95 weight percent of a nonionic monomer comprising from 1 to 3 members independently selected from the group consisting of the following monomers:

| acrylamide (AM) | vinylacetate (VA) |
|---|---|
| N-alkylacrylamide (NAAM) | vinyl alcohol (VOH) |
| | acrylate esters |
| methacrylamide (MAM) | allyl alcohol (AAlc) |

(b) from at least 5 to as much as 80 weight percent of a cationic monomer comprising 1 or 2 members independently selected from the group consisting of the following monomers:
   dimethyldiallylammonium chloride (DMDAAC)
   diallylamine (DAA)
   methyldiallylamine (MDAA)

N,N-dialkyldiallylammonium chloride
dimethylaminoethylmethacrylate (DMAEM)
methacyloyloxyethyl trimethylammonium chloride (METAC)
methacyloyloxyethyl trimethylammonium metyl sulfate (METAMS)
acryloyloxyethyl trimethylammonium chloride (AETAC)
dimethylaminopropylmethacrylamide (DMAPMA)
methacrylamidopropyl trimethylammonium chloride (MAPTAC)

and (c) from at least 1 to as much as 75 weight percent of an anionic monomer comprising 1 or 2 members independently selected from the group consisting of the following monomers:
acrylic acid (AA)
methacrylic acid (MAA)
2-acrylamido-2-methylpropanesulfonic acid (AMPSA)
crotonic acid (CA)
sodium vinyl sulfonate (SVS)
acrylamidoglycolic acid (AGly)
2-acrylamido-2-methylbutanoic acid (AMBA)
2-acrylamido-2-methylpropanephosphonic acid (AMPPA)
sodium vinyl phosphonate (SVP)
allyl phosphonic acid.

7. A method according to claim 6 wherein the amount of the cationic and anionic components is such that the overall % net charge of the ampholyte terpolymer is between −5.0 and +5.0.

8. A method according to claim 6 wherein the weight percent of the nonionic component is from 10 to 80, the weight percent of the cationic component is from 15 to 60, and the weight percent of the anionic component is from 5 to 40.

9. A method according to claim 6 wherein the ampholyte terpolymer is a member selected from the group consisting of:

| | |
|---|---|
| AM/DMDAAC/AGly | acrylate esters/DMDAAC/AA |
| AM/DMDAAC/AMBA | AM/DMDAAC/AA/AMPSA/AMPPA |
| AM/DMDAAC/APA | acrylate esters/DMDAAC/AMBA |
| AM/DMDAAC/AMPPA | AM/DMDAAC/SVP |
| AAlc/DMDAAC/AA | |
| AM/MDAA/AA | |
| MAM/METAMS/MAA | |
| | AM/DMDAAC/AETAC/AA |
| | AM/DMDAAC/DMAEM/AA |
| AM/DMDAAC/MAA | AM/MAPTAC/AA |
| AM/DMDAAC/CA | |
| AM/DMDAAC/SVS | |
| AM/DAA/AA | AM/MAM/DMDAAC/AA |
| AM/DAA/MAA | AM/NAAM/DMDAAC/AA |
| AM/DMAEM/AA | AM/DAA/AMPSA |
| AM/AETAC/AA | AM/VA/VOH/DMDAAC/AA |
| AM/METAMS/MAA. | |

10. A method according to claim 6 wherein the ampholyte terpolymer has a molecular weight of from about 500 thousand to about 5 million.

11. A method according to claim 6 wherein the cosmetically acceptable medium is an anionic surfactant-containing shampoo.

12. A method according to claim 6 wherein the amount of ampholyte terpolymer contained in the cosmetically acceptable medium is from 0.5 to 5.0% by weight.

13. A method of treating hair in conjunction with the shampooing thereof with an anionic surfactant-containing shampoo, so as to improve the conditioning thereof with respect to the properties of detangling, wet combability, wet feel, dry combability, dry feel, sheen, static flyaway control, and curl retention, comprising applying to said hair a composition compatible with said anionic surfactant-containing shampoo such that a clear formulation thereof is provided without the loss of said conditioning properties, wherein said composition comprises a cosmetically acceptable medium containing from 0.1–10% by weight of a water soluble ampholyte terpolymer having a weight average molecular weight of from about 10 thousand to 10 million, comprising:

(a) from at least 1 to as much as 95 weight percent of a nonionic monomer comprising from 1 to 3 members independently selected from the group consisting of the following monomers:

| | |
|---|---|
| acrylamide (AM) | vinylacetate (VA) |
| N-alkylacrylamide (NAAM) | vinyl alcohol (VOH) |
| | acrylate esters |
| methacrylamide (MAM) | allyl alcohol (AAlc) |

(b) from at least 5 to as much as 80 weight percent of a cationic monomer comprising 1 or 2 members independently selected from the group consisting of the following monomers:
dimethyldiallylammonium chloride (DMDAAC)
diallylamine (DAA)
methyldiallylamine (MDAA)
N,N-dialkyldiallylammonium chloride
dimethylaminoethylmethacrylate (DMAEM)
methacyloyloxyethyl trimethylammonium chloride (METAC)
methacyloyloxyethyl trimethylammonium metyl sulfate (METAMS)
acryloyloxyethyl trimethylammonium chloride (AETAC)
dimethylaminopropylmethacrylamide (DMAPMA)
methacrylamidopropyl trimethylammonium chloride (MAPTAC)

and (c) from at least 1 to as much as 75 weight percent of an anionic monomer comprising 1 or 2 members independently selected from the group consisting of the following monomers:
acrylic acid (AA)
methacrylic acid (MAA)
2-acrylamido-2-methylpropanesulfonic acid (AMPSA)
crotonic acid (CA)
sodium vinyl sulfonate (SVS)
acrylamidoglycolic acid (AGly)
2-acrylamido-2-methylbutanoic acid (AMBA)
2-acrylamido-2-methylpropanephosphonic acid (AMPPA)
sodium vinyl phosphonate (SVP)
allyl phosphonic acid.

14. A method according to claim 13 wherein the amount of the cationic and anionic components is such that the overall % net charge of the ampholyte terpolymer is between −5.0 and +5.0.

15. A method according to claim 13 wherein the weight percent of the nonionic component is from 10 to 80, the weight percent of the cationic component is from 15 to 60, and the weight percent of the anionic component is from 5 to 40.

16. A method according to claim 13 wherein the ampholyte terpolymer is a member selected from the group consisting of:

| | |
|---|---|
| AM/DMDAAC/AGly | acrylate esters/DMDAAC/AA |
| AM/DMDAAC/AMBA | AM/DMDAAC/AA/AMPSA/AMPPA |
| AM/DMDAAC/APA | acrylate esters/DMDAAC/AMBA |
| AM/DMDAAC/AMPPA | AM/DMDAAC/SVP |
| AAlc/DMDAAC/AA | |
| AM/MDAA/AA | |
| MAM/METAMS/MAA | |
| | AM/DMDAAC/AETAC/AA |
| | AM/DMDAAC/DMAEM/AA |
| AM/DMDAAC/MAA | AM/MAPTAC/AA |
| AM/DMDAAC/CA | |
| AM/DMDAAC/SVS | |
| AM/DAA/AA | AM/MAM/DMDAAC/AA |
| AM/DAA/MAA | AM/NAAM/DMDAAC/AA |
| AM/DMAEM/AA | AM/DAA/AMPSA |
| AM/AETAC/AA | AM/VA/VOH/DMDAAC/AA |
| AM/METAMS/MAA. | |

17. A method according to claim 13 wherein the ampholyte terpolymer has a molecular weight of from about 500 thousand to about 5 million.

18. A method according to claim 13 wherein the cosmetically acceptable medium is an anionic surfactant-containing shampoo.

19. A method according to claim 13 wherein the amount of ampholyte terpolymer contained in the cosmetically acceptable medium is from 0.5 to 5.0% by weight.

* * * * *